US011981714B2

(12) United States Patent
Castor et al.

(10) Patent No.: US 11,981,714 B2
(45) Date of Patent: May 14, 2024

(54) CCR5 AND CD4 siRNA-TARGETED PHOSPHOLIPID NANOSOMES THERAPEUTICS FOR TREATMENT OF HIV-1 AND OTHER DISEASES

(71) Applicants: Trevor Percival Castor, Arlington, MA (US); Vasudevacharya Jayarama, Framingham, MA (US); James A McSwiggen, Boulder, CO (US)

(72) Inventors: Trevor Percival Castor, Arlington, MA (US); Vasudevacharya Jayarama, Framingham, MA (US); James A McSwiggen, Boulder, CO (US)

( * ) Notice: Subject to any disclaimer, the term of this patent is extended or adjusted under 35 U.S.C. 154(b) by 341 days.

(21) Appl. No.: 17/096,738

(22) Filed: Nov. 12, 2020

(65) Prior Publication Data

US 2022/0144629 A1 May 12, 2022

(51) Int. Cl.

| | |
|---|---|
| ***C07K 14/54*** | (2006.01) |
| ***B82Y 5/00*** | (2011.01) |
| ***B82Y 40/00*** | (2011.01) |
| ***C12N 15/113*** | (2010.01) |

(52) U.S. Cl.
CPC ............ *C07K 14/5446* (2013.01); *B82Y 5/00* (2013.01); *B82Y 40/00* (2013.01); *C12N 15/113* (2013.01)

(58) Field of Classification Search
CPC ...... C07K 14/5446; B82Y 5/00; B82Y 40/00; C12N 15/113
See application file for complete search history.

*Primary Examiner* — Robert S Cabral

(57) ABSTRACT

The present invention pertains to the nanoencapsulation of siRNA and other biologics in phospholipid nanosomes for the improved delivery of siRNA and other biologics to targeted diseased human or animal organs and human or animal cells and apparatus and methods for making the same. In embodiments of the present invention, novel siRNAs were designed to down regulate CCR5 and CD4, based on an analysis of all known alternative transcripts for each gene from both human and monkey (*Macaca mulatta*) genomes. Embodiments of the present invention feature supercritical, critical and near critical fluids. Embodiments of the present invention also pertain to down regulation of CXCR4 receptor and targeting of nanosomes containing specific siRNA sequences to cells expressing those receptors on the cell surface by coating them with specific ligands. These include ligands for the receptors CCR5, CD4 and CXCR4.

26 Claims, 3 Drawing Sheets

Specification includes a Sequence Listing.

| Upper | Standards |
|---|---|
| Lane 1 | DNA Ladder (100bp) |
| Lane 3 | Pure CCR5-854_siRNA - 1,232 ng |
| Lane 4 | Pure CCR5-854_siRNA - 616 ng |
| Lane 5 | Pure CCR5-854_siRNA - 308 ng |
| Lane 6 | Pure CCR5-854_siRNA - 154 ng |
| Lane 7 | Pure CCR5-854_siRNA - 77 ng |
| Lane 8 | Pure CCR5-854_siRNA - 38.5 ng |
| Lane 9 | Pure CCR5-854_siRNA - 19.3 ng |
| Lane 10 | Pure CCR5-854_siRNA - 9.6 ng |
| Lane 11 | Pure CCR5-854_siRNA - 4.8 ng |
| Lane 12 | Pure CCR5-854_siRNA - 2.4 ng |

| Lower | Nanosomal Extracts |
|---|---|
| Lane 1 | DNA Ladder (100bp) |
| Lane 3 | RNA-i-11 - Empty |
| Lane 4 | RNA-i-15 - Negative_siRNA |
| Lane 5 | RNA-i-21 - CCR5-854_siRNA |
| Lane 6 | RNA-i-22 - CD4-583_siRNA |
| Lane 7 | RNA-i-25 - CCR5-982_siRNA |
| Lane 8 | RNA-i-28 - CD4-1175_siRNA |
| Lane 9 | RNA-i-27 - CCR5-1170_siRNA |
| Lane 10 | RNA-i-26 - CD4-569_siRNA |
| Lane 11 | RNA-i-30 - CCR5-1301_siRNA + RANTES protein |

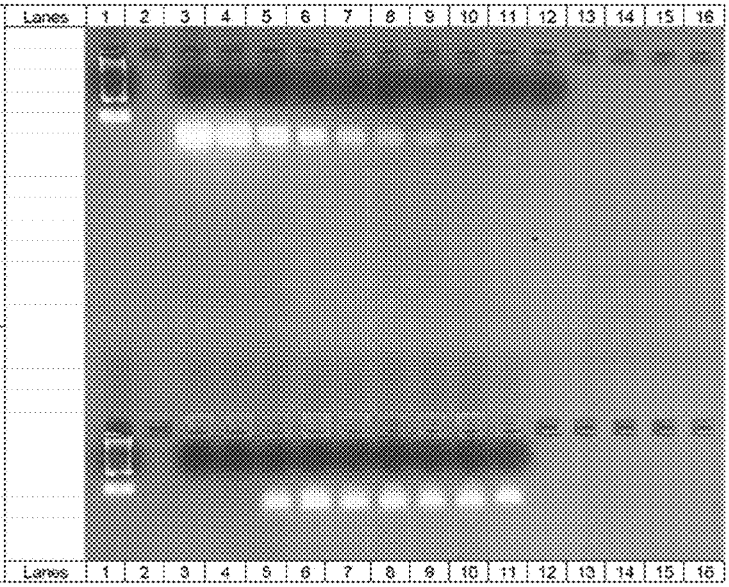

*Fig. 2*

CCR5 AND CD4 siRNA-TARGETED PHOSPHOLIPID NANOSOMES THERAPEUTICS FOR TREATMENT OF HIV-1 AND OTHER DISEASES

FEDERAL SUPPORT

Research leading to this invention was in part funded with government support awarded by National Institute of Allergy and Infectious Diseases, NIH, DHHS.

INCORPORATION BY REFERENCE

Electronicc computer readable text file "CCR5_CD4_Sequence.txt" (created on Feb. 4, 2021 and having 763 bytes) is herein incorporated by reference in its entirety and made a part hereof, replacing prior versions of the sequence listings. No new matter is included.

FIELD OF THE INVENTION

The present invention pertains to the nanoencapsulation of siRNA and other biologics in targeted phospholipid nanosomes for the improved delivery of siRNA and other biologics to diseased human or animal organs and human or animal cells and apparatus and methods for making the same.

BACKGROUND OF THE INVENTION

More than 35 million people have died from AIDS to date, and another 37 million people are living with HIV/AIDS worldwide. In the United States, an estimated 1.2 million people are currently living with HIV and approximately 40,000 infections occur each year. There is no vaccine against HIV, and the associated AIDS, if untreated, will lead to the death of over 95% of infected individuals ~10 years post-infection. HIV-1 infects several cell types and the infected persons must remain life-long on combination antiretroviral therapy (cART).

Current cART medications have multiple long-term adverse effects such as: (i) rapid emergence of pools of drug-specific resistance HIV mutants that are not responsive to treatment; (ii) drug toxicity; (iii) drug/pill burden that often cause non-adherence; and (iv) high lifetime economic costs. These drawbacks hamper the success of these limited treatment options. Indeed, evidence show that complete viral suppression can be achieved by just one or two fully active select anti-HIV drugs, yet conventional cART must include 3-line regimens to assure long-term or non-reversal of efficacy. Some of these medications, like the fusion/entry inhibitor Enfuvirtide (Fuzeon), also exhibit poor bioavailability due to their relative insolubility in an aqueous environment such as blood.

Therefore, the need for alternative therapeutic approaches/strategies that are efficacious but with lesser of these limitations becomes an urgent discovery question that continues to remain a critical challenge to global public health and HIV/AIDS response agencies. RNA-based therapeutics hold great promise in the progress towards alternative HIV treatment. Specifically, small interfering ribonucleic acid (hereinafter referred to as siRNA) has widely been demonstrated to protect hosts from viruses and transposons, making this evolutionary conserved double-stranded RNA an important candidate for therapeutic intervention. But full harnessing of RNA as therapeutics is significantly impeded by the lack of appropriate delivery strategies that ensure RNA stability and potency in humans. Nanosomal formulation of siRNA and small molecules offers a potential avenue to improving efficacy of these compounds.

The following naming convention will be followed in this invention for the different siRNAs—X_siRNA, where X is the protein whose expression is silenced. For example, CCR5_siRNA silences the expression of CCR5 protein. Since multiple siRNAs can bind to different regions of the mRNA, each siRNA is named as X-n_siRNA, where n refers to the first nucleotide in the mRNA sequence for the protein to which the siRNA binds. For example, CCR5-654_siRNA is designed to bind to a region that begins with nucleotide number 654 on the CCR5 mRNA molecule.

Nanosomes present a novel frontier for Virus-Free Delivery—(VFD) of RNA and alternative therapeutics. There is wide consensus that non-viral delivery of RNA has intersecting positive attributes. siRNAs are small size oligonucleotides with immense potential to silence HIV in direct transfection experiments in vitro. Encapsulation in nanosomes provide a delivery matrix to bypass impediments like product degradation due to instability, safety concerns due to replicative risks of viral delivery vectors, toxicity associated with larger dosing for desired effect, and limited potency due to restricted tissue distribution.

Moreover, RNA-based products have the greater potential to hasten scale-up of on-demand manufacturing, can be delivered directly into the cytoplasm where gene expression can be suppressed without the need for nuclear localization, and interact directly with host innate defense system to stimulate or regulate specific outcomes. Progress has been made in chemical-based delivery strategies using liposomes, molecular-sized chemical conjugates, and supramolecular nanocarriers. However, nucleic acids per se are relatively large, negatively charged polymers, and significant clinical challenges from the standpoint of delivery to cells still persist. Thus, although RNA-based therapeutics hold great promise for HIV prevention and treatment, delivery and stability-related obstacles still need to be overcome to hasten clinical use.

Exploiting the inherent thermodynamic properties of supercritical fluid solvents (SFS), a novel technology can be used for formulating small-to-medium size nanoparticles (100-300 mu) that use purely physical methods. This novel technology can be paired with novel RNA-therapeutic strategy using specific siRNA molecules, to manufacture and test delivery efficiency, stability and potency of these therapeutics. Furthermore, encapsulation of siRNA molecules in smaller widely distributed nanosomes represent a valuable pharmacological innovation opportunity to facilitate product discovery and efficacy evaluation that will revolutionize HIV therapeutics and prevention. Nanosomal siRNA (nano_siRNA) has the increased potential to penetrate tissue barriers to confer potent silencing of specific genes that promote HIV infection.

Additionally, the nano_siRNA can be co-encapsulated with other protein or pharmacologic therapeutic products to enhance or broaden antiviral activity of the primary molecule. These RNA nanosomes can be effective at nano concentrations that mitigate systemic toxicities. Pegylation can be introduced during encapsulation and manufacturing to increase (i) nano_siRNA biological residence time, (ii) subsequent therapeutic efficacy and (iii) overall therapeutic index.

Additionally, the nanoparticles encapsulated with siRNA can be coated with proteins or small molecules that bind to specific receptors on specific types of cells. This would result in a targeted delivery of the drugs to the desired types of cells.

The present invention relates to small interfering ribonucleic acids (hereinafter referred to as siRNAs). siRNAs are small double stranded RNA molecules, usually 20 to 25 nucleotides in length which bind to other nucleic acids, interfere with and silence expression events. siRNAs are used to study gene expression and disease states involving gene expression events. siRNAs have utility in controlling of gene expression at the cellular level to treat disease. However, siRNA have been limited by difficulty in placing the RNA inside the cells.

It is difficult to make liposomes of a size that permits absorption or other delivery of siRNA to the interior of cells. Liposomes having a diameter measured in nanometers, from about 10 to 500 nanometers, are referred to as nanosomes. Nanosomes have potential as a delivery vehicle for siRNA. However, it is difficult to make nanosomes with consistent and high load of an agent such as siRNA. Processes for loading an agent do not necessarily permit the recycling of the agent not incorporated into the liposomes resulting in a loss of the agent and higher costs of manufacture.

SUMMARY OF THE INVENTION

In embodiments of the present invention, novel siRNAs were designed to down-regulate CCR5 and CD4, based on an analysis of all known alternative transcripts for each gene from both human and monkey (*Macaca mulatta*) genomes. The siRNA fragments were designed in three steps according the following parameters: fragment frequency; gene region; % GC content; and miRNA seed. The selected siRNAs met all of the design constraints in this first step. In a second design step, the candidate 19-mer fragments were searched against the monkey alternative transcripts and scored for the closest homology to the human sequence. All of the selected siRNAs had 100% sequence homology between all of the human and monkey alternative transcripts. In the final design step, the candidate 19-mer fragments were evaluated for potential non-specific activity against the rest of the human/monkey genomes. The selected sequences had fewer than 160 13-mer hits in the case of CD4 and fewer than 120 hits in the case of CCR5.

Further embodiments of the present invention are directed to an apparatus and methods for making nucleic acid loaded nanosomes, particularly for encapsulating siRNA fragments of the type described. One embodiment of the present invention directed to an apparatus which comprises of a first containment means for containing a mixture of an aqueous solution of nucleic acid and a phospholipid solution with a supercritical, critical or near critical fluid. The apparatus further comprises of an injection means in fluid communication with said first containment means for receiving the mixture and releasing the mixture as a stream into a decompression liquid. The apparatus further comprises of a decompression vessel in fluid communication with the injection means for holding a decompression liquid and receiving the mixture as a stream. The stream forms one or more nanosomes loaded with a nucleic acid in the decompression liquid.

As used above, the term "nucleic acid" refers to deoxyribonucleic acid (DNA) or ribonucleic acid (RNA). These nucleic acids may have any sequence desired. One embodiment of the present invention is directed to siRNA.

Embodiments of the present invention feature supercritical, critical and near critical fluids. A compound becomes critical at conditions that equal both its critical temperature and critical pressure. A compound becomes supercritical at conditions that equal or exceeds both its critical temperature and critical pressure. As used herein, the term near critical is used to denote a compound that approaches one or both critical temperature and critical pressure, but is not a critical or supercritical fluid. These parameters are intrinsic thermodynamic properties of all sufficiently stable pure compounds and mixtures. Carbon dioxide, for example, becomes a supercritical fluid at conditions that equal or exceed its critical temperature of 31.1° C. and its critical pressure of 72.8 atm (1,070 psig). As a supercritical fluid, normally gaseous substances, such as carbon dioxide, become dense phase fluids that have been observed to exhibit greatly enhanced solvating power.

At a pressure of 3,000 psig (204 atm) and a temperature of 40° C., carbon dioxide has a density of approximately 0.8 g/cc and exhibits properties similar to those of a nonpolar solvent such as hexane, having a dipole moment of zero Debye. A supercritical, critical or near critical fluid has a wide spectrum of solvation power, as its density is strongly dependent upon temperature and pressure. Temperature changes of tens of degrees or pressure changes by tens of atmospheres can change a compound's solubility in a supercritical, critical or near critical fluid by an order of magnitude or more. Temperature and pressure allow the fine-tuning of solvation properties and the fractionation of mixed solutes. The selectivity of nonpolar supercritical, critical and near critical fluids can be influenced by the addition of compounds known as modifiers, entrainers and co-solvents. These modifiers are typically more polar, such as acetone, ethanol and methanol.

One embodiment of the present invention features a circulation loop in fluid communication with the first containment means. The circulation loop is for forming the phospholipid solution with a supercritical, critical or near critical fluid. One embodiment of a circulation loop has a solids vessel for holding a phospholipid and forming a suspension of phospholipid and a supercritical, critical or near critical fluid. Another embodiment of a circulation loop has a mixing chamber in communication with said solids vessel for receiving the suspension of phospholipid and a supercritical, critical or near critical fluid and forming the phospholipid solution with a supercritical, critical or near critical fluid.

One embodiment of a circulation loop has a return means in fluid communication with the mixing chamber and the solids vessel for returning a suspension or solution of a phospholipid with a super critical, critical or near critical fluid from the mixing chamber to the solids vessel to increase the phospholipid content of the suspension of phospholipids and a super critical, critical or near critical fluid. One embodiment of a circulation loop has one or more pumps to move the suspension or solution of a phospholipid and a super critical, critical or near critical fluid through the solids vessel and mixing chamber.

A preferred circulation loop is in fluid communication with a source of supercritical, critical or near critical fluid.

One embodiment of the apparatus features a first containment means in fluid communication with an siRNA source. For example, the siRNA source holds an siRNA in a buffer. One preferred buffer is a low ionic strength buffer.

One embodiment of the apparatus features containment means in the form of one or more conduits, vessels and an inline mixer.

A further embodiment of the present invention, directed to a method of forming a nucleic acid loaded nanosomes comprises the step of forming a mixture of an aqueous solution of a nucleic acid and a phospholipid solution with a supercritical, critical or near critical fluid in a first containment means. Next, the method comprises the step of directing the mixture to injection means in fluid communication with the first containment means and releasing the mixture as a stream into a decompression liquid held in a decompression vessel in fluid communication with the injection means. And, the method comprises the step of forming one or more nanosomes loaded with a nucleic acid in the decompression liquid.

One embodiment features a nucleic acid which is an siRNA.

One embodiment of the method features specific siRNAs which down-regulate or silence the expression of specific HIV receptor or coreceptors, including but not limited to, CD4, CCR5 and CXCR4.

One embodiment of the method features the further step of forming the phospholipid solution with a supercritical, critical or near critical fluid in a circulation loop. The circulation loop is in fluid communication with the first containment means. One circulation loop has a solids vessel for holding a phospholipid and forming a suspension of phospholipid and a supercritical, critical or near critical fluid. One circulation loop has a mixing chamber in communication with the solids vessel for receiving the suspension of phospholipid and a supercritical, critical or near critical fluid and forming the phospholipid solution with a supercritical, critical or near critical fluid.

One circulation loop has return means in fluid communication with the mixing chamber and the solids vessel for returning a suspension or solution of a phospholipid with a supercritical, critical or near critical fluid from the mixing chamber to the solids vessel to increase the phospholipid content of the suspension of phospholipid and a super critical, critical or near critical fluid. The method further comprising the step of circulating said suspension or solution of a phospholipid with a supercritical, critical or near critical fluid. A preferred circulation loop has one or more pumps to move the suspension or solution of a phospholipid and a supercritical, critical or near critical fluid through the solids vessel and mixing chamber. One embodiment of the present method features a circulation loop in fluid communication with a source of supercritical, critical or near critical fluid.

One embodiment features a first containment means in fluid communication with an siRNA source. A preferred siRNA source holds an siRNA in a buffer. And, a preferred buffer is a low ionic strength buffer. One method comprises the step of forming a buffered solution of an siRNA.

One embodiment of the method features containment means having one or more conduits, vessels and inline mixers.

A further embodiment of the present invention is directed to, as an article of manufacture, nanosomes comprising a phospholipid and an siRNA with trace amounts of a low ionic strength buffer.

In an additional embodiment, the nanoparticle encapsulated with a CCR5_siRNA is coated with CCL5, aka RANTES protein which is a CC chemokine with a molecular weight of 7,900 that competes with HIV gp120 to bind CCR5, a co-receptor for HIV. Coating CCL5 on nanosomes will be achieved by incorporating phosphatidylethanolamine into the lipid bilayer during synthesis of the nanosomes. The ethanolamine on the surface of the nanosomes will then be cross-linked to the lysine residues in the RANTES protein by glutaraldehyde or other amine cross-linking chemistries. CCL5 is a natural ligand produced in the human body and CCR5 is one of its receptors. CCR5 serves as a co-receptor on cells that also express CD4 and together, the two molecules make the cells permissible to HIV infection. Hence, targeting to CD4+ cells expressing CCR5 protein will be provided by the presence of CCL5 on the surface of the nanoparticles which would protect such cells from HIV infection by the down regulation of expression of CCR5 by the CCR5_siRNA.

In an additional embodiment, the nanoparticle encapsulated with a CCR5_siRNA is coated with an alternative natural ligand for CCR5. These include MIP-1α (aka CCL3), MIP-1β (aka CCL4) and MCP-2 (aka CCL8). Of these, CCL4 is particularly advantageous since its only known receptor is CCR5, which makes it highly specific for only the cells expressing CCR5. This specificity is not provided by the other natural ligands of CCR5 mentioned here since they can bind to one or few other receptors in addition to CCR5.

In an additional embodiment, the nanoparticle encapsulated with CCR5_siRNA is coated with a small molecule inhibitor of HIV binding to CCR5 such as Maraviroc or with truncated or altered CCL5, which compete with HIV binding to CCR5 with a higher efficiency than CCL5. Since Maraviroc is a hydrophobic compound poorly soluble in water, coating of the siRNA nanoparticle will be performed by simple mixing which allows the compound to bind to the siRNA nanosomes by hydrophobic interactions. The truncated or altered CCL5 proteins are coated onto the siRNA by the same methodology as the one described above for CCL5.

In an additional embodiment, the nanoparticle encapsulated with a CXCR4_siRNA is coated with SDF1, aka CXCL12 protein which is a 72 amino acid long CXC chemokine with a molecular weight of 8,522 that competes with HIV gp120 to bind CXCR4, a co-receptor for HIV. CXCL12 is a natural ligand produced in the human body and CXCR4 is one of its receptors. CXCR4 serves as a co-receptor on cells that also express CD4 and together, the two molecules make the cells permissible to infection by CXCR4-tropic HIV. Hence, targeting to CD4+ cells expressing CXCR4 protein will be provided by the presence of CXCL12 on the surface of the nanosomes which would protect such cells from HIV infection by the down regulation of expression of CXCR4 by the CXCR4_siRNA.

In an additional embodiment, the nanoparticle encapsulated with CXCR4_siRNA is coated with an alternate ligand for CXCR4. These include the different isoforms of CXCL12, 7 of which have been identified so far, and Plerixafor, a small molecule inhibitor of CXCL12 binding to CXCR4. The methodology for coating these alternative ligands will be the same as the ones described above for CCL5. The methodology described for coating the proteins on the surface of siRNA can also be used to coat Plerixafor since Plerixafor has a number of amine groups which can be used for cross linking with the ethanolamine head groups present on the surface of siRNA.

In an additional embodiment, the nanoparticle encapsulated with CD4_siRNA is coated with mature IL16 protein, a natural ligand for human CD4, which is 121 amino acids long with a molecular weight of 12.4 KD (Sigma-Aldrich). CD4 is the natural receptor for HIV and, therefore, down regulation of CD4 expression on the cell surface will make the cells resistant to HIV. Hence, specific delivery to CD4+ cells will be provided by the presence of mature IL16 on the surface of the nanosomes which would protect such cells from HIV infection by the down regulation of expression of CD4 by the CD4_siRNA.

These and other features and advantages of the present invention will be apparent to those skilled in the art upon viewing the figure which is described briefly below and upon reading the detailed description that follows.

BRIEF DESCRIPTION OF THE DRAWING

FIG. 2 depicts 3.5% agarose gel for nanosomal siRNA

DETAILED DESCRIPTION OF THE INVENTION

Embodiments of the present invention are described in detail as an apparatus and methods for making nucleic acid loaded nanosomes in which the nucleic acid is siRNA. The description represents the best mode known to the inventor and is subject to further alteration and modification without departing from the teachings herein. Therefore, the present discussion should not be considered limiting.

Figure 1:
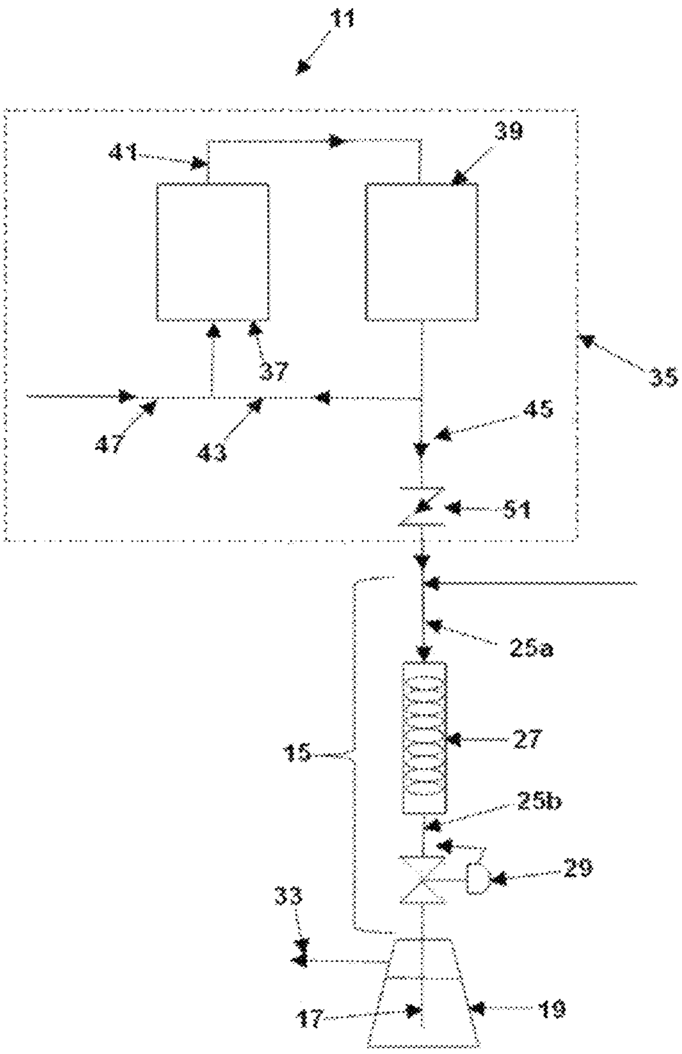
FIG. 1 depicts a schematic representation of an apparatus embodying features of the present invention.

Turning now to FIG. 1, an apparatus having features of the present invention, generally designated by the numeral 11, is depicted. Apparatus 11 comprises three major elements: a first containment means 15, injection means 17 and decompression vessel 19. Apparatus 11 can be made of any size depending on the amount of nanosomes desired from the processes. Materials for making elements of the apparatus 11 are rigid with strength to contain pressures and temperatures used to maintain supercritical, critical or near critical conditions. A preferred material is a metal such as stainless steel.

The first containment means 15 is comprised of conduits 25*a* and 25*b*, in-line mixer 27 and a pressure regulator 29. First containment means is for containing a mixture of an aqueous solution of a nucleic acid and a phospholipid solution with a supercritical, critical or near critical fluid. Other embodiments of the first containment means 15 may comprise additional features such as vessels [not shown]. The conduit 25*a* receives an aqueous solution of nucleic acid; and the conduit receives a phospholipid solution with a supercritical, critical or near critical fluid. The aqueous solution and the phospholipid solution are directed into the in-line mixer to form a mixture. The mixture is directed into conduit 25*b* and maintained at an appropriate pressure by the pressure regulator 29.

Injection means 17 is in fluid communication with the first containment means 15 via conduit 25*b* for receiving the mixture and releasing the mixture as a stream into a decompression liquid. Injection means 17 comprises one or more nozzles having opening for releasing the mixture which appear as bubbles in a decompression liquid described in greater detail in a later discussion. The size of the openings and the flow of the mixture influence the size of the nanosomes formed. One embodiment of injection means 17 is a 10-mil (internal diameter of 0.25 mm or 250 micron) capillary injection nozzle. Larger internal diameter 316 stainless steel capillary tubes can be used to manufacture larger particle sizes. Impingement nozzles (Bete Fog Nozzle, Inc., Greenfield, Mass.) can also be used.

Decompression vessel 19 is in fluid communication with the injection means 17. Decompression vessel 19 holds a decompression liquid and openings of injection means are held under the decompression liquid to allow the mixture to be released as a stream with the gas of the super critical, critical or near critical fluid bubbling to the surface. Decompression vessel 19 has an opening [not shown] or vent 33 for venting or discharging the gas. The stream forms one or more nanosomes loaded with a nucleic acid in the decompression liquid.

Apparatus 11 further comprises a circulation loop 35. Circulation loop 35 comprises a solids vessel 37, a mixing vessel 39, a feed conduit 41, a return conduit 43 and an exit conduit 45. Circulation loop 35 is in fluid communication with a source of gas at a pressure and temperature consistent with a supercritical, critical or near critical fluid or such gas and the phospholipids are brought to such conditions in the circulation loop 35. As depicted, circulation loop 35 receives a gas through source conduit 47 under super critical, critical or near critical temperatures and pressure at a junction or "T" in return conduit 43. Those skilled in the art will immediately recognize that source conduit 45 may be introduced at any point in circulation loop 35.

Circulation loop 35 is in fluid communication the first containment means 15 via exit conduit 45. Exit conduit 45 has a valve 51 to direct fluids through the exit conduit and into the first containment means 15 or through the return conduit 43. The circulation loop 35 is for forming a phospholipid solution with a supercritical, critical or near critical fluid. The solids vessel 37 holds a phospholipid and forms a suspension or solution of phospholipid and a supercritical, critical or near critical fluid. Mixing chamber 39 is in fluid communication with solids vessel 37 via the feed conduit 41 for receiving the suspension of phospholipid and a supercritical, critical or near critical fluid and forming the phospholipid solution with a supercritical, critical or near critical fluid.

Return means in the form of return conduit 43 is in fluid communication with the mixing chamber 39 and the solids vessel 37 for returning a suspension or solution of a phospholipid with a supercritical, critical or near critical fluid from the mixing chamber 39 to the solids vessel 37. The returning fluid removes more phospholipid from the solids vessel 37 to increase the phospholipid content of the solution or suspension of phospholipid and a super critical, critical or near critical fluid.

Preferably, the circulation loop 35 has one or more pumps [not shown] known in the art to move the suspension or solution of a phospholipid and a super critical, critical or near critical fluid through the solids vessel 37, mixing chamber 39, return conduit 43 and feed conduit 41.

Embodiments of the present method will now be described with respect to the operation of the apparatus 11. The method will be described with respect to forming nucleic acid loaded nanosomes. A mixture of an aqueous solution of a nucleic acid and a phospholipid solution with a supercritical, critical or near critical fluid is formed in a first containment means 15. The mixture is directed to injection means 17 in fluid communication with the first containment means 15. Injection means 17 releases the mixture as a stream into a decompression liquid held in a decompression vessel 19. One or more nanosomes loaded with a nucleic acid is formed in the decompression liquid.

In a further step, the phospholipid solution with a supercritical, critical or near critical fluid is formed in a circulation loop 35. Phospholipids held in solids vessel 37 are carried as a solution or suspension of phospholipid and a supercritical, critical or near critical fluid via feed conduit 41 to mixing vessel 39 to form the phospholipid solution with a supercritical, critical or near critical fluid.

Return means in the form of return conduit 43 in fluid communication with the mixing chamber and the solids vessel returns a suspension or solution of a phospholipid with a supercritical, critical or near critical fluid from the mixing chamber to the solids vessel to increase the phospholipid content of the suspension of phospholipids and a supercritical, critical or near critical fluid. The fluids are circulated to increase the phospholipid content of the solution ultimately leaving the circulation loop 35 via exit conduit 45.

Article of manufacture made by apparatus 11 and the methods herein described are nanosomes comprising a phospholipid and a nucleic acid with trace amounts of a low ionic strength buffer. One preferred nucleic acid is siRNA.

Features of the present invention are further exemplified in the Examples that follow.

EXAMPLES

Example 1: siRNA Design and Specifications siRNAs designed to down regulate CCR5 and CD4 expression are based on an analysis of all known alternative transcripts for each gene from both human and monkey (*Macaca mulatta*) genomes. Sequences used in the example are listed in Table 1.

TABLE 1

Transcripts Used in siRNA Design

| Organism | GenBank Acc # | Description |
|---|---|---|
| *Homo sapiens* | NM_000579.3 | *Homo sapiens* C-C motif chemokine receptor 5 (gene/pseudogene) (CCR5), transcript variant A, mRNA. |
| *Homo sapiens* | NM_001100168.1 | *Homo sapiens* C-C motif chemokine receptor 5 (gene/pseudogene) (CCR5), transcript variant B, mRNA. |
| *Macaca mulatta* | NM_001042773.3 | *Macaca mulatta* C-C motif chemokine receptor 5 (CCR5), transcript variant 2, mRNA. |
| *Macaca mulatta* | NM_001309402.1 | *Macaca mulatta* C-C motif chemokine receptor 5 (CCR5), transcript variant 1, mRNA. |
| *Macaca mulatta* | XM_015131082.1 | PREDICTED: *Macaca mulatta* chemokine (C-C motif) receptor 5 (CCR5), transcript variant X1, mRNA. |
| *Homo sapiens* | NM_000616.4 | *Homo sapiens* CD4 molecule (CD4), transcript variant 1, mRNA. |
| *Homo sapiens* | NM_001195014.2 | *Homo sapiens* CD4 molecule (CD4), transcript variant 2, mRNA. |
| *Homo sapiens* | NM_001195015.2 | *Homo sapiens* CD4 molecule (CD4), transcript variant 3, mRNA. |
| *Homo sapiens* | NM_001195016.2 | *Homo sapiens* CD4 molecule (CD4), transcript variant 4, mRNA. |
| *Homo sapiens* | NM_001195017.2 | *Homo sapiens* CD4 molecule (CD4), transcript variant 5, mRNA. |
| *Homo sapiens* | XM_017020228.1 | PREDICTED: *Homo sapiens* CD4 molecule (CD4), transcript variant X1, mRNA. |
| *Macaca mulatta* | NM_001042662.1 | *Macaca mulatta* CD4 molecule (CD4), mRNA. |
| *Macaca mulatta* | XM_015150817.1 | PREDICTED: *Macaca mulatta* CD4 molecule (CD4), transcript variant X1, mRNA. |
| *Macaca mulatta* | XM_015150818.1 | PREDICTED: *Macaca mulatta* CD4 molecule (CD4), transcript variant X2, mRNA. |
| *Macaca mulatta* | XM_015150819.1 | PREDICTED: *Macaca mulatta* CD4 molecule (CD4), transcript variant X3, mRNA. |
| *Macaca mulatta* | XM_015150820.1 | PREDICTED: *Macaca mulatta* CD4 molecule (CD4), transcript variant X4, mRNA. |
| *Macaca mulatta* | XM_015150821.1 | PREDICTED: *Macaca mulatta* CD4 molecule (CD4), transcript variant X5, mRNA. |

siRNA design was performed in three steps. In the first step, the human transcripts were split into all possible 19-mer fragments and scored by the following parameters.

a) Fragment frequency. A count of the number of alternative transcripts that contain the 19-mer sequence. The goal was to find 19-mers that match 100% of the alternative transcripts.

b) Gene region. Whether the siRNA matches 5'UTR, 3'UTR or CDS. This is largely informational. SiRNAs matching the CDS or 3'UTR tend to be most successful, but matching other regions also yields active siRNAs.

c) % GC content. Most active siRNAs have a GC content between 30 and 50%, although sequences with more or less % GC can be active as well.

d) miRNA Seed. This parameter warns if the seed sequence of the siRNA (positions 2-7 or 2-8 of the antisense strand) is also present in known miRNAs. If so, it increases the chance that the siRNA will act as a miRNA to generate activity against other genes.

All of the selected siRNAs met all of the design constraints in this first step.

In a second design step, the candidate 19-mer fragments were searched against the monkey alternative transcripts and scored for the closest homology to the human sequence. All of the selected siRNAs had 100% sequence homology between all of the human and monkey alternative transcripts.

In the final design step, the candidate 19-mer fragments were evaluated for potential activity against other genes. The 19-mers were searched against a database of fragment frequencies for all 13-mer sequences in the human genome. A 13-mer sequence was chosen because that represents roughly the shortest stable binding unit for sequences in the concentration ranges in which we operate. Thus, it is possible for a 13-mer portion of a 19-mer siRNA to bind to an unintended transcript and stimulate non-specific activity. 13-mer fragments with low occurrence in the human genome (1-300 hits) are considered to be less likely to display non-specific activity than those with high occurrences (up to 3.6 million hits for some sequences). The selected sequences had fewer than 160 13-mer hits in the case of CD4 and fewer than 120 hits in the case of CCR5. Note that this non-specific activity analysis is an interim step; a more extensive analysis will be carried out on the lead candidates.

The top 10 sequences chosen for initial testing are listed in Table 2. There are an additional 28 CD4 sequences and 81 CCR5 sequences that meet all of the design criteria and are available as back-up candidates.

TABLE 2 siRNA Sense-Strand Sequences Chosen for Initial Testing

| Gene | Position | Sequence |
|---|---|---|
| CCR5 | 654 | AAUGUGUCAACUCUUGACA |
| CCR5 | 720 | CCUGACAAUCGAUAGGUAC |
| CCR5 | 982 | GUCAUGGUCAUCUGCUACU |
| CCR5 | 1170 | CUCUAACAGGUUGGACCAA |
| CCR5 | 1301 | ACAUUGCCAAACGCUUCUG |
| CD4 | 563 | AAGACUCAGAUACUUACAU |
| CD4 | 569 | CAGAUACUUACAUCUGUGA |
| CD4 | 844 | AAAAUAGACAUCGUGGUGC |
| CD4 | 1159 | CUUGAAGCGAAAACAGGAA |
| CD4 | 1175 | GAAAGUUGCAUCAGGAAGU |

Example 2: Nanoencapsulation of CCR5_siRNA and CD4_siRNA in SFS-CFN Phospholipid Nanosomes Based on embodiments described above, we nanoencapsulated CCR5_siRNAs and CD4_siRNAs listed in Table 2 in phospholipid nanosomes utilizing the SFS-CFN co-injection process and characterized them for particle size and absorbance at 260 nm and 280 nm. The results are listed in Table 3.

The specific conditions used for each of the preparations are as follows:

In RNA-I-21, siRNA nanosomes were made using PC 16:0/16:0 DPPC and PEG-2000 DSPE for targeted molar ratio of 27:1 using SFS Propane:Ethanol::80:20 at P=3,000 psig and T=40° C., 0.01" injector into 10% sucrose buffer at 4° C. and pH=7.0, a feed of RNA buffer containing DSPE PEG-2000 and CCR5-654_siRNA, and co-injection ratio (SFS:Feed) ratio of 1.0. RNA-I-21 was conducted with 1.43 nanomoles/mL CCR5-654_siRNA.

RNA-I-22 through RNA-I-30 were conducted with 1.43 nanomoles/mL, the same siRNA concentration and similar conditions that were utilized for RNA-I-21 (CCR5-654_siRNA).

RNA-I-62 through RNA-I-64 included the addition of the cationic lipid MVL-5 to the targeted molar ratio of 27:1::PC 16:0/16:0 DPPC:PEG-2000 DSPE, and were conducted at the same conditions as RNA-I-21 through RNA-I-30.

TABLE 3

Particle Sizes and Absorbance of CCR5_siRNA and CD4_siRNA in SFS-CFN Phospholipid Nanosomes

| Sample | siRNA | Particle Size (nm) | Absorbance (260 nm) | Absorbance (280 nm) |
|---|---|---|---|---|
| Sigma 100 nm Std. | NA | 111 | NA | NA |
| RNA-I-21-01-03 | CCR5-654 | 143 | 0.486 | 0.359 |
| RNA-I-22-01-03 | CD4-563 | 136 | 0.135 | 0.078 |
| RNA-I-25-01-03 | CCR5-982 | 207 | NM | NM |
| RNA-I-26-01-03 | CD4-1175 | 187 | 0.751 | 0.616 |
| RNA-I-27-01-03 | CCR5-1170 | 156 | 0.236 | 0.177 |
| RNA-I-28-01-03 | CD4-569 | 123 | 0.015 | 0.007 |
| RNA-I-29-01-03 | RANTES Protein | 146 | 0.744 | 0.718 |
| RNA-I-30-01-03 | RANTES Protein with CCR5-1301 | 140 | 1.002 | 0.878 |
| RNA-I-62-01-03 | CD4-844 | 144 | 0.189 | 0.128 |
| RNA-I-63-01-03 | CCR5-720 | 170 | 0.129 | 0.099 |
| RNA-I-64-01-03 | CD4-1159 | 204 | 0.203 | 0.151 |

Figure 3:
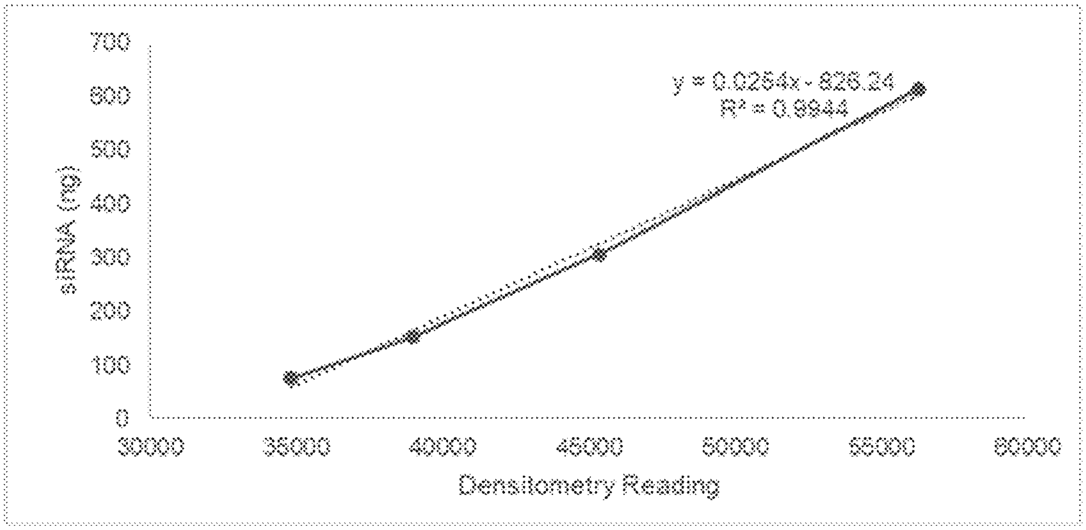
FIG. 3 depicts standard OD curve of pure CCR5-654_siRNA

Example 3: siRNA Quantification and Quality Assessment siRNA quantification and quality assessment were used to measure the amounts of siRNA in 9 of the ten nanosomal preparations used in efficacy testing listed in the sample index of FIG. 2 (RNA-I-29-01-03 was prepared using the RANTES protein instead of siRNA). Briefly, 100 mg of each freeze-dried sample was solubilized with ethanol, dried and resuspended in 100 μL of siRNA buffer. These were then diluted 1:3, and 15 μL loaded per lane of a 3.5% agarose gel. The bands were analyzed by densitometry using the ImageJ software. A standard curve was generated from the serial dilutions of non-encapsulated (pure) CCR5-654_siRNA (FIG. 3) and the amounts per lane calculated. The amounts per lane were then used to calculate the amount recovered in the total amount of freeze-dried material for Fraction 01. Percent nanoencapsulation efficiency in Fraction 01 out of the total siRNA used in the nanosomal run was then calculated. The amount of siRNA used for each nanosomal run was about 21.5 nanomoles (approximately 280 μg).

A picture of the gel run along with the list of samples is shown as FIG. 2. The upper half was used for the CCR5-654_siRNA standards and the lower half was used for the extracted nanosomal siRNA samples. The standard curve generated for the linear range of the assay shown in FIG. 3 along with the linear equation was used to calculate the amounts of siRNA in each lane. The readings obtained for the sample bands, the calculated amounts per band and total recovery in Fraction 01 of the input siRNA are listed in Table 4. RNA-I-11 (empty nanosomes with no siRNA) showed an absence of siRNA as expected. The results in Table 4 indicate nanoencapsulation efficiencies ranging from 60 to 152%.

TABLE 4

Readings Obtained, Calculated Amounts and Nanoencapsulation Efficiencies of Nanosomal siRNAs

| Sample | Reading | Amount in Band (ng) | Mass of Fraction I (mg) | Amount in Fraction I (μg) | Expected Amount in Fraction I (μg) | Recovery in Fraction I (%) |
|---|---|---|---|---|---|---|
| RNA-I-11 - Empty | — | NA | | NA | NA | NA |
| RNA-I-15 - Negative_siRNA | — | NA | | NA | NA | NA |
| RNA-I-21 - CCR5-654_siRNA | 49241 | 424 | 2381 | 202 | 133 | 152% |
| RNA-I-22 - CD4-563_siRNA | 44192 | 296 | 891 | 53 | 50 | 106% |
| RNA-I-25 - CCR5-982_siRNA | 43234 | 272 | 3960 | 215 | 222 | 97% |
| RNA-I-26 - CD4-1175_siRNA | 44209 | 297 | 3179 | 189 | 178 | 106% |
| RNA-I-27 - CCR5-1170_siRNA | 42193 | 245 | 2874 | 141 | 161 | 88% |
| RNA-I-28 - CD4-569_siRNA | 46017 | 343 | 2778 | 190 | 156 | 122% |
| RNA-I-30 - CCR5-1301_siRNA + RANTES protein | 39097 | 167 | 2140 | 71 | 120 | 60% |

The above experiment (RNA-I-55) was repeated in RNA-I-60 using two siRNAs as standards—CCR5-1301_siRNA and CCR5-654_siRNA, to verify and confirm the results of RNA-I-55. Standard curves were generated from the serial dilutions of non-encapsulated CCR5-654_siRNA and CCR5-1301_siRNA, and the amounts per lane calculated by each curve. These were then used to calculate nanoencapsulation efficiencies in Fraction 01. The nanoencapsulation efficiencies of the input siRNAs for the nanosomes samples ranged from 40 to 107% (data not shown). This was a little lower than the prior experiment; this difference was probably the result of sample degradation.

Example 4: Knockdown Study of CD4_siRNA Nanosomes Against HIV-1 NL4-3 Virus

Three CD4_siRNA nanosomes along with a negative_siRNA control and an empty nanosomes control were tested in an HIV infectivity knock down study by BFU assay, as follows (Expt. RNA-I-50b).

MAGI P4/R5 cells carry the β-galactosidase gene under control of the HIV LTRs. Hence, infection of these cells by HIV expressing tat gene results in expression of β-galactosidase activity which can be monitored by staining the cells with X-gal which turns them blue. Briefly, 96 well plates of MAGI P4/R5 cells were infected with HIV-1 and fixed 2-3 days post infection with a fixative containing 1% formaldehyde and 0.2% glutaraldehyde. Fixed cells were washed with PBS and stained for β-galactosidase activity using X-gal at 1 mg/mL in PBS with 5 mM potassium ferricyanide and 5 mM potassium ferrocyanide as per published procedures. The cells were usually stained 3 hours to overnight, the number of blue foci counted under the microscope and reported as Blue Focus-forming Units (BFUs).

Transfections were performed using 5 and 10 μL of nanosomes with a constant amount of 0.5 μL of lipofectamine. Only CD4_siRNA nanosomes were tested in this experiment since HIV-1 NL4-3 uses CXCR-4 as the co-receptor and therefore, the CCR5_siRNAs would not be expected to be functional. 1 day after transfection, the cells were infected with HIV-1 NL4-3 virus and stained 2 days post infection for β-galactosidase activity. The percent reduction in BFUs compared to the negative control are listed in Table 5.

Table 5 shows that the two CD4_siRNA preparations, RNA-I-22 (CD-4-563_siRNA) and RNA-I-28 (CD4-569_siRNA) showed dose dependent protection from HIV-1 infection compared to negative siRNA across both the levels tested. RNA-I-22 (CD4-563_siRNA) was more potent with 95% inhibition with 10 μL and 72% inhibition with 5 μL. RNA-I-28 (CD4-569_siRNA) showed less inhibition with 73% and 42% respectively at the two levels.

TABLE 5

Percent Inhibition HIV-1 NL4-3 Virus by CD4-siRNA Nanosomes vs Negative_siRNA Nanosomes

| | | Dose Per Well | |
|---|---|---|---|
| Experiment | siRNA | 5 μL | 10 μL |
| RNA-I-20 | Negative siRNA | 0% | 0% |
| RNA-I-22 | CD4-563_siRNA | 72% | 95% |
| RNA-I-28 | CD4-569_siRNA | 42% | 73% |

These results indicate that both of the two CD4_siRNAs inhibit HIV infection.

Example 5: Knockdown Study of CCR5_siRNA and/or RANTES Protein Nanosomes Against HIV-1 BaL Virus In this experiment (RNA-I-51), nanosomal formulations of 3 CCR5_siRNAs, RANTES protein and RANTES protein co-encapsulated with a CCR5_siRNA, were evaluated using the β-galactosidase assay for the ability to inhibit HIV-1 BaL virus infection, since this strain is CCR5 tropic. The procedure was the same as the previous experiment with HIV-1 NL4-3 except that the nanosomes were tested at a single level of 10 μL mixed with 0.5 μL of lipofectamine. Results are reported in Table 6.

The results indicate that all the five formulations inhibited HIV-1 infection with high efficacy. RNA-I-25 (CCR5-982_siRNA), RNA-I-29 (RANTES alone) and RNA-I-30 (RANTES with CCR5-1301_siRNA) showed almost complete inhibition whereas RNA-I-21 (CCR5-654_siRNA) and RNA-I-27 (CCR5-1170_siRNA) showed slightly reduced efficacy of 85%.

The results indicate that HIV-1 BaL virus infection of P4/R5 cells was inhibited by all CCR5_siRNA nanosomes as well as RANTES protein nanosomes with high efficacy.

TABLE 6

No. of BFUs of HIV-1 BaL Virus Obtained and Percent Inhibition vs Negative_siRNA Nanosomes after CCR5_siRNA and/or RANTES Nanosomes Mediated Knockdown

| Experiment | siRNA | # BFUs | % Reduction |
|---|---|---|---|
| RNA-I-21 | CCR5-654_siRNA | 7 | 85% |
| RNA-I-25 | CCR5-982_siRNA | 0 | 100% |
| RNA-I-27 | CCR5-1170_siRNA | 7 | 85% |
| RNA-I-29 | RANTES Protein | 1 | 98% |
| RNA-I-30 | CCR5-1301_siRNA + RANTES | 2 | 96% |
| RNA-I-20 | Negative_siRNA | 47 | 0% |
| RNA-I-11 | Empty Nanosomes | 22 | NA |

Example 6: Knockdown Study of CD4_siRNA, CCR5_siRNA and RANTES Protein Nanosomes Against HIV-$1_{RF}$ Virus In this study (RNA-I-47), 8 siRNA nanosomal formulations and 2 controls were evaluated for HIV-1 inhibition on P4/R5 cells using the BFU assay. The test formulations were the same 3 CD4_siRNAs, 3 CCR5_siRNAs, RANTES protein alone and RANTES protein co-encapsulated with a CCR5_siRNA in phospholipid nanosomes, tested previously in RNA-I-50b and RNA-I-51. The HIV-1 virus used was NIH ARP Cat #2804, a member of a panel HIV-$1_{RF}$ viruses and is dual-tropic with the ability to infect both CCR5 and CXCR4 receptor expressing cells.

This study was similar to the previous studies with a few differences. The ratio of nanosomes and lipofectamine was much higher at 10 μL to 3 μL respectively, and log dilutions of the samples were tested to determine dose-dependent responses. Serial log dilutions of an antiviral cocktail of 10 μM Raltegravir and 1 μM Efavirenz (approximately 1000× the respective published $ID_{50}$ for the compounds when tested individually) were also tested as a process control.

The number of BFUs obtained at different dilutions of nanosomes and the antiviral cocktail are listed in Table 7. The data in Table 7 indicates a dose dependent reduction in the number of BFUs for the antiviral cocktail (positive control), with 46 BFUs for the untreated control and 0 BFUs for log dilutions 2, 1 and undiluted. The data for the antiviral cocktail was used to generate a dose-response curve and to calculate the Inhibitory $Dose_{50}$ ($ID_{50}$) of the cocktail. The data demonstrates that the assay process is suitable since the calculated $ID_{50}$ of the cocktail was 1.6 nM for Raltegravir and 0.16 nM for Efavirenz.

The data in Table 7 indicates a reduction in the number of BFUs for only the undiluted and log 1 dilutions for all nanosomal treatments, including empty nanosomes and negative_siRNA, suggesting possible cytotoxicity by the undiluted nanosomes, lipofectamine or both. The reduction was much higher for the undiluted samples with only one blue cell present for the negative_siRNA formulation. Almost 100% of the unstained cells were rounded (dead) at this dilution, possibly due to non-specific cytotoxicity. The number of BFUs obtained for log 1 dilution were reduced to varying extents for the 8 test formulations compared to the number seen for the negative RNA sample. The number of rounded cells was only 30-50% for this dilution. Hence, the reduction of number of blue cells by the test formulations compared to the negative_siRNA formulation for this dilution were used to calculate the efficacy as % reduction in HIV-1 infectivity.

TABLE 7

Number of HIV-1 BFUs Obtained After CD4_siRNA, CCR5_siRNA and RANTES Protein Nanosomes Mediated Knockdown

| | | Log Dilution | | | | | |
|---|---|---|---|---|---|---|---|
| Expt. | siRNA | Undiluted | 1 | 2 | 3 | 4 | Control |
| Anti-Viral cocktail | Raltegravir + Efavirenz | 0 | 0 | 0 | 9 | 27 | 46 |
| RNA-I-11 | Empty | 10 | 30 | 25 | 31 | 37 | 37 |
| RNA-I-15 | Negative | 1 | 22 | 53 | 46 | 45 | 39 |
| RNA-I-21 | CCR5-654 | 3 | 12 | 41 | 49 | 67 | 38 |
| RNA-I-22 | CD4-563 | 0 | 0 | 29 | 64 | 54 | 49 |
| RNA-I-25 | CCR5-982 | 5 | 14 | 70 | 58 | 65 | 50 |
| RNA-I-26 | CD4-1175 | 0 | 3 | 75 | 61 | 57 | 27 |
| RNA-I-27 | CCR5-1170 | 0 | 11 | 54 | 81 | 51 | 47 |
| RNA-I-28 | CD4-569 | 0 | 12 | 50 | 54 | 63 | 48 |
| RNA-I-29 | RANTES | 4 | 19 | 46 | 55 | 65 | 35 |
| RNA-I-30 | CCR5-1301 + RANTES | 1 | 19 | 52 | 42 | 41 | 42 |

The calculated % reductions for log dilution 1 are listed in Table 8. The results in Table 8 indicate that complete or almost complete inhibition of HIV-1 infection was shown by RNA-I-22 (CD4-563_siRNA) and RNA-I-26 (CD4-1175_siRNA) nanosomes; moderate inhibition in the 20-80% range by RNA-I-21 (CCR5-654_siRNA), RNA-I-25 (CCR5-982_siRNA), RNA-I-27 (CCR5-1170_siRNA) and RNA-I-28 (CD4-569_siRNA) nanosomes; and low to no inhibition by RNA-I-29 (RANTES protein alone) and RNA-I-30 (RANTES protein with CCR5-1301_siRNA) nanosomes.

These results are different from those obtained in RNA-I-50b for the CD4_siRNA nanosomes and RNA-I-51 for CCR5_siRNA and RANTES nanosomes, since a high level of efficacy was seen for all the preparations in those two experiments with the possible exception of RNA-I-26 (CD4-1175_siRNA). The different results could be due to the lower levels of lipofectamine used in those experiments, higher dilution (log 1) results used for analysis and the virus strains used. In contrast to the earlier experiments, a 6-fold higher level of lipofectamine was used in this experiment.

TABLE 8

Percent Reduction in HIV Infectivity by siRNA Formulations at Log 1 Dilution Compared to the Negative_siRNA Formulation

| Experiment | siRNA | # BFUs | % Reduction |
|---|---|---|---|
| RNA-I-15 | Negative | 22 | 0% |
| RNA-I-21 | CCR5-654 | 12 | 45% |
| RNA-I-22 | CD4-563 | 0 | 100% |
| RNA-I-25 | CCR5-982 | 14 | 36% |
| RNA-I-26 | CD4-1175 | 3 | 86% |
| RNA-I-27 | CCR5-1170 | 11 | 50% |
| RNA-I-28 | CD4-569 | 12 | 45% |
| RNA-I-29 | RANTES | 19 | 14% |
| RNA-I-30 | CCR5-1301 + RANTES | 19 | 14% |

Example 7: Knockdown Study of Nanosomal Formulations of CD4_siRNA, CCR5_siRNA and RANTES Protein Against HIV-$1_{RF}$ Virus with and without Lipofectamine A knockdown study (RNA-I-61) of the 8 nanoencapsulated and the corresponding unencapsulated (naked) siRNA preparations along with two controls described in the previous experiments was performed using freshly reconstituted materials with HIV-1 RF, NIH Cat #2804, diluted to contain ~100 Blue Focus forming Units (BFUs) per dose of inoculum. The previous experiments with this virus demonstrated efficacy by some siRNAs, but the data was not sufficient to calculate the Inhibitor Dose at 50% inhibition ($ID_{50}$). The objective of this experiment was to test a range of concentrations of the inhibitors to determine the $ID_{50}$ for each preparation based on the siRNA content. Since the nanosomal materials were freshly reconstituted, they were recharacterized.

The reconstituted samples were characterized in terms of particle size. siRNA quantifications of nanosomal and naked siRNAs were performed by UV spectrophotometry and by agarose gel analysis. The siRNA quantification data by agarose gel analysis was used to calculate the $ID_{50}$ values where possible.

The reconstituted samples as well as the naked siRNA preparations were tested for virus infection inhibitory activity. The inhibition of infectivity was measured by counting the number of blue foci due to the induced β-galactosidase activity in the host MAGI P4/R5 cells by the infecting HIV. This infectivity assay showed good titers for the virus controls with the number of BFUs ranging from 30-92. Majority of the wells infected with virus only in the absence of any treatment showed BFUs in the 50-60 range (data not shown). The number of BFUs for each treatment at various dilutions were used to calculate the % inhibition from the corresponding dilution for the Negative_siRNA samples. The inhibitor activity was also quantified by measuring the p24 antigen concentration in each of the wells.

Particle Size Analyses: Particle size analyses were performed by Coulter N4-MD particle size analyzer as previously described. The results listed in Table 9 indicate that all the preparations had particle sizes in the desired range of 100 to 200 nm.

TABLE 9

Particle Sizes of Reconstituted Nanosomal Preparations

| Experiment | siRNA | Mean Diameter (nm) |
|---|---|---|
| RNA-I-10 | Empty | 197 |
| RNA-I-14 | Negative | 92 |
| RNA-I-21 | CCR5-654 | 218 |
| RNA-I-22 | CD4-563 | 115 |
| RNA-I-25 | CCR5-982 | 89 |
| RNA-I-26 | CD4-1175 | 171 |
| RNA-I-27 | CCR5-1170 | 102 |
| RNA-I-28 | CD4-569 | 42 |
| RNA-I-29 | RANTES | 81 |
| RNA-I-30 | CCR5-1301 + RANTES | 150 |

RNA Quantification by UV Spectrophotometry: Nanosomal preparations and the corresponding non-encapsulated siRNA samples were quantified by measuring absorption at OD260. In addition, OD280 values were measured to determine the OD260/OD280 ratio, an indicator of RNA purity in clean preparations. The starting material for nanosomal preparations was the freeze-dried material of Fraction 01 in the encapsulation process. The theoretical concentration of siRNAs in the freeze-dried material reconstituted to the original volume was calculated to be 0.43 nanomoles/mL (=5.72 μg/mL) based on the amount of siRNA input for the encapsulation process. For the Negative_siRNA, the amount was calculated to be 1.5 picomoles/mL (=20 ng/mL). Non-encapsulated siRNAs for each nanosomal preparation were spiked into 10% sucrose at the same concentration (0.43 nanomoles/mL).

The nanosomal preparations and the spiked pure siRNAs were each mixed with equal volumes of ethanol to release the encapsulated siRNAs. The OD260 and OD280 values were determined using the same matrix as the blank. A standard curve was generated in the same matrix using pure transfer siRNA. The readings were used to determine the amount of siRNA, OD260/280 ratios and percent recovery vs the theoretical concentration of siRNA based on a concentration of 0.43 nanomoles/mL.

The results indicated that the OD260/280 ratios of the Pure_siRNAs ranged from 1.708 to 1.971 for different siRNA samples. The recoveries for Pure_siRNAs ranged from 67% to 170% of the spiked amounts for the test siRNAs (data not shown).

For the nanosomal_siRNAs, the OD260/280 ratios ranged from 1.097 to 1.33 indicating interference of lipid components with absorbance measurements. The recoveries for the nanosomal_siRNAs were also high with all exceeding 200%, some of which may be caused by the interference of the lipid components of the nanosomal preparations with siRNA estimation (data not shown).

RNA Quantification by Agarose Gel Analysis: The nanosomal and Pure_siRNA sample aliquots used for spectrophotometry were also analyzed on 3.5% agarose gels, as described in previous reports. All the samples were subjected to a release process to recover the encapsulated siRNAs. The release process consisted of drying the reconstituted materials in a Speed Vac followed by dissolution in ethanol. The ethanol was then removed by Speed Vac and the residual material was suspended in a small volume of siRNA buffer and run on 3.5% ethidium bromide-agarose gels. Suitable standards were run in parallel and the band intensities were measured by densitometry using ImageJ software. The results are listed in Table 10 for Pure_siRNA and Table 11 for nanosomal siRNA.

The data for Pure_siRNA in Table 10 indicates recoveries higher than the expected 100% at between 137% and 298%. However, the data for nanosomal siRNA in Table 11 indicates that the recoveries for the nanosomal_siRNAs range from 76% to 220% with most of the values being less than 200%. These results suggest that this is a better method for the quantification of siRNAs than the UV spectrophotometric method for the estimation of $ID_{50}$ values.

TABLE 10

Percent Recoveries for Pure_siRNAs by Gel Analysis

| Experiment | siRNA | Densitometry Signal | Amt. of RNA (ng/mL) | Recovery (%) |
|---|---|---|---|---|
| Matrix Alone | Empty equivalent | no band | no RNA | NA |
| RNA-I-14 | Negative | no band | no RNA | NA |
| RNA-I-21 | CCR5-654 | 25824 | 10067 | 176% |
| RNA-I-22 | CD4-563 | 30688 | 13780 | 241% |
| RNA-I-25 | CCR5-982 | 28550 | 12070 | 211% |
| RNA-I-26 | CD4-1175 | 22420 | 7843 | 137% |
| RNA-I-27 | CCR5-1170 | 27102 | 10981 | 192% |
| RNA-I-28 | CD4-569 | 34433 | 17070 | 298% |
| RNA-I-29 | RANTES Protein | no band | no RNA | NA |

TABLE 10-continued

Percent Recoveries for Pure_siRNAs by Gel Analysis

| Experiment | siRNA | Densitometry Signal | Amt. of RNA (ng/mL) | Recovery (%) |
|---|---|---|---|---|
| RNA-I-30 | CCR5-1301 + RANTES Protein | 29045 | 12456 | 218% |

TABLE 11

Percent Recoveries for Nanosomal_siRNAs by Gel Analysis

| Experiment | siRNA | Densitometry Signal | Amt. of RNA (ng/mL) | Recovery (%) |
|---|---|---|---|---|
| Matrix Alone | Empty equivalent | no band | no RNA | NA |
| RNA-I-14 | Negative | no band | no RNA | NA |
| RNA-I-21 | CCR5-654 | 21281 | 7168 | 125% |
| RNA-I-22 | CD4-563 | 29197 | 12575 | 220% |
| RNA-I-25 | CCR5-982 | 15654 | 4341 | 76% |
| RNA-I-26 | CD4-1175 | 22583 | 7943 | 139% |
| RNA-I-27 | CCR5-1170 | 17841 | 5339 | 93% |
| RNA-I-28 | CD4-569 | 20131 | 6522 | 114% |
| RNA-I-29 | RANTES Protein | no band | no RNA | NA |
| RNA-I-30 | CCR5-1301 + RANTES Protein | 17265 | 5064 | 89% |

Infectivity Assay by BFUs: The percent inhibitions obtained with various Nanosomal_siRNA formulations versus Negative_siRNA formulations in the presence of lipofectamine are listed in Table 12.

Data in Table 12 indicate that significant dose-dependent inhibition of formation of blue foci was seen for the CD4-563_siRNA and CD4-1175_siRNA by nanosomal preparations in the presence of lipofectamine. Moderate inhibitions at only lower dilutions of the treatments were also seen for CCR5-654_siRNA, CCR5-1301_siRNA+RANTES protein and CD4-569_siRNA. There were some similar results seen with Naked_siRNA treatments in the presence of lipofectamine as listed in Table 13. However, in most cases, the nanosomal preps performed much better as shown for CD4-1175_siRNA, CD4-569_siRNA, CCR5-1301_siRNA+ RANTES protein and RANTES protein alone. Negative numbers are shown as zero since stimulation by the siRNAs are not anticipated. Negative numbers could be due to the variation in the number of blue cells counted in the corresponding controls.

TABLE 12

Inhibition of BFUs by Various Nanosomal_siRNA Formulations vs Negative_siRNA Nanosomes in the Presence of Lipofectamine

| | | Treatment Dilutions | | | | |
|---|---|---|---|---|---|---|
| Expt. | siRNA | 1 | 5 | 15 | 45 | 135 |
| RNA-I-14 | Negative | 0% | 0% | 0% | 0% | 0% |
| RNA-I-21 | CCR5-654 | 63% | 47% | 56% | 0% | 21% |
| RNA-I-22 | CD4-563 | 97% | 89% | 75% | 17% | 40% |
| RNA-I-25 | CCR5-982 | 16% | 0% | 0% | 0% | 38% |
| RNA-I-26 | CD4-1175 | 97% | 89% | 78% | 46% | 0% |
| RNA-I-27 | CCR5-1170 | 9% | 22% | 2% | 0% | 28% |
| RNA-I-28 | CD4-569 | 72% | 22% | 0% | 0% | 0% |
| RNA-I-29 | RANTES | 25% | 20% | 16% | 0% | 30% |
| RNA-I-30 | CCR5-1301 + RANTES | 72% | 35% | 11% | 20% | 46% |

TABLE 13

Inhibition of BFUs by Various Naked_siRNA vs Negative_siRNA in the Presence of Lipofectamine

| | | Treatment Dilutions | | | | |
|---|---|---|---|---|---|---|
| Expt. | siRNA | 1 | 5 | 15 | 45 | 135 |
| RNA-I-14 | Negative | 0% | 0% | 0% | 0% | 0% |
| RNA-I-21 | CCR5-654 | 67% | 52% | 28% | 2% | 26% |
| RNA-I-22 | CD4-563 | 87% | 91% | 85% | 42% | 26% |
| RNA-I-25 | CCR5-982 | 0% | 0% | 0% | 0% | 0% |
| RNA-I-26 | CD4-1175 | 60% | 100% | 90% | 53% | 43% |
| RNA-I-27 | CCR5-1170 | 0% | 0% | 0% | 0% | 0% |
| RNA-I-28 | CD4-569 | 0% | 25% | 0% | 56% | 43% |
| RNA-I-29 | RANTES | 0% | 34% | 18% | 0% | 0% |
| RNA-I-30 | CCR5-1301 + RANTES | 0% | 34% | 8% | 7% | 0% |

However, in the absence of lipofectamine, the nanosomal formulations showed moderate inhibitor activity (Table 14) with outstanding performances by CD4-563_siRNA, CD4-569_siRNA and CCR5-982_siRNA, and possibly CD4-1175_siRNA. CCR5-982_siRNA outperformed its naked version and its nanoencapsulated version with lipofectamine.

TABLE 14

Inhibition of BFUs by Various Nanosomal_siRNA Formulations vs Negative_siRNA Nanosomes in the Absence of Lipofectamine

| | | Treatment Dilutions | | | | |
|---|---|---|---|---|---|---|
| Expt. | siRNA | 1 | 5 | 15 | 45 | 135 |
| RNA-I-14 | Negative | 0% | 0% | 0% | 0% | 0% |
| RNA-I-21 | CCR5-654 | 33% | 35% | 0% | 0% | 1% |
| RNA-I-22 | CD4-563 | 63% | 28% | 0% | 3% | 3% |
| RNA-I-25 | CCR5-982 | 50% | 23% | 0% | 0% | 35% |
| RNA-I-26 | CD4-1175 | 4% | 50% | 0% | 0% | 4% |
| RNA-I-27 | CCR5-1170 | 0% | 38% | 0% | 0% | 3% |
| RNA-I-28 | CD4-569 | 42% | 48% | 0% | 0% | 8% |
| RNA-I-29 | RANTES | 33% | 18% | 0% | 2% | 10% |
| RNA-I-30 | CCR5-301 + RANTES | 25% | 18% | 0% | 0% | 10% |

These results indicate that CD4_siRNA and CCR5-siRNA formulations are quite active in inhibiting HIV-1 RF infections, and nanoencapsulation improves their inhibition activities.

p24 Antigen Assay for Nanosomal_siRNA Treatments: p24 antigen assay was performed for supernatants from infected cells harvested at the time of β-galactosidase assay using ABL HIV-1 p24 ELISA kits. The results are listed as % inhibitions at each dose level compared to the p24 antigen titers for the Negative_siRNA nanosomes in Table 15.

TABLE 15

Inhibition of p24 Antigen Production by Various Nanosomal_siRNA Formulations vs Negative_siRNA Nanosomes in the Presence of Lipofectamine

| | | Treatment Dilutions | | | | |
|---|---|---|---|---|---|---|
| Expt | siRNA | 1 | 5 | 15 | 45 | 135 |
| RNA-I-14 | Negative | 0% | 0% | 0% | 0% | 0% |
| RNA-I-21 | CCR5-654 | 99% | 66% | 0% | 13% | 56% |
| RNA-I-22 | CD4-563 | 104% | 68% | 43% | 33% | 27% |
| RNA-I-25 | CCR5-982 | 53% | 0% | 0% | 62% | 66% |
| RNA-I-26 | CD4-1175 | 135% | 112% | 48% | 61% | 2% |
| RNA-I-27 | CCR5-1170 | 70% | 91% | 0% | 14% | 10% |

TABLE 15-continued

| Inhibition of p24 Antigen Production by Various Nanosomal_siRNA Formulations vs Negative_siRNA Nanosomes in the Presence of Lipofectamine | | | | | | |
|---|---|---|---|---|---|---|
| | | Treatment Dilutions | | | | |
| Expt | siRNA | 1 | 5 | 15 | 45 | 135 |
| RNA-I-28 | CD4-569 | 52% | 37% | 0% | 0% | 6% |
| RNA-I-29 | RANTES | −31% | 57% | 0% | 50% | 0% |
| RNA-I-30 | CCR5-1301 + RANTES | 59% | 38% | 0% | 44% | 7% |

Table 15 indicates levels of inhibitions that are very similar to those seen for the BFU assay listed in Table 13. High levels of inhibition were seen for CD4-563_siRNA and CD4-1175_siRNA and moderate levels of efficacy were seen for CCR5-654_siRNA, CCR5-1301_siRNA+RANTES protein and CD4-569_siRNA. In addition, CCR5-1170_siRNA also appeared to show inhibition at treatment dilutions of undiluted and 1:5. These results confirm the results of the BFU assay.

50% Inhibitory Dose ($ID_{50}$) Values: The data from RNA quantification using gel analysis and the infectivity results were used to plot dose response curves and calculate the $ID_{50}$ (a.k.a. Inhibitory Concentration that results in 50% inhibition, [$IC_{50}$]) values. The calculated $ID_{50}$ values for nanosomal preparations in the presence of lipofectamine are listed in Table 16.

TABLE 16

| 50% Inhibitory Dose ($ID_{50}$) Values of Nanosomal siRNAs in the Presence of Lipofectamine | | |
|---|---|---|
| Expt. | siRNA | 50% Inhibitory Dose ($ID_{50}$) (nM) |
| RNA-I-22 | CD4-563 | 3.0 |
| RNA-I-26 | CD4-1175 | 1.1 |
| RNA-I-28 | CD4-569 | 21.3 |
| RNA-I-30 | CCR5-1301 + RANTES | 13.5 |
| RNA-I-21 | CCR5-564 | 12.3 |

The results in Table 16 indicate that nanosomal preparations of CD4-563_siRNA and CD4-1175_siRNA are active at low nM range in the presence of lipofectamine. The three other preparations, CD4-569_siRNA, CCR5-1301_siRNA with RANTES protein and CCR5-654_siRNA also show some efficacy which is about 4 to 20 times less effective than the first two preparations. These results indicate that nanoencapsulation preserves the efficacy of siRNAs while providing the potential advantages of stability and protection from degradation in vivo.

The above results show that CD4_siRNAs showed high to moderate levels of inhibition against HIV-1 RF strain either in pure form or nanoencapsulated form. CCR5_siRNAs showed moderate or no inhibitory activity. This is consistent with the dual-tropism of HIV-1 RF which is the ability to use either of CCR5 or CXCR4 coreceptors for infections. MAGI P4/R5 cells are susceptible to infection by CXCR4-tropic viruses. Hence, HIV-1 RF is able to infect these cells even if the expression of CCR5 coreceptors is suppressed by siRNA treatment, by utilizing the CXCR4 receptors. However, since CD4 is the primary receptor, HIV-1 RF is not able to bypass this receptor when its expression is inhibited.

Example 8: Summary of Nano_siRNA Studies

A summary of the results of all the studies performed are shown in Table 17. In some cases, as shown by the last 2 columns of Table 17, Lipofectamine decreased knockdown efficiency (RNA-I-27, RNA-I-25 and RNA-I-28) whereas in other cases, Lipofectamine increased knockdown efficiency (RNA-I-21, RNA-I-22, RNA-I-26, RNA-I-29 and RNA-I-30). CD4_siRNA nanosomes inhibited infections at $ID_{50}$ of 1.1 nM and 3.0 nM. One preparation of CCR5_siRNA nanosomes showed an $ID_{50}$ of 12.3 nM and a preparation of CCR5_siRNA co-encapsulated with RANTES protein showed an $ID_{50}$ of 13.5 nM. The higher numbers of $ID_{50}$ for CCR5_siRNA nanosomes is consistent with the dual tropism of HIV-1 RF strain.

TABLE 17

| Summary of HIV-1 Knockdown Efficiency by BFU assay on P4/R5 Cells | | | | | | | |
|---|---|---|---|---|---|---|---|
| | | RNA-I-51 | RNA-I-50b | RNA-I-54 | RNA-I-47 | RNA-I-61 | RNA-I-61 |
| | | Nano + Lipo | Nano + Lipo | Nano + Lipo | Nano + Lipo | Nano + Lipo | Nano − Lipo |
| | | 10 µL | 10 µL | 1:5 | 1:10 | 1:5 | 1:5 |
| Expt. | siRNA | BaL | NL4-3 | RF | RF | RF | RF |
| RNA-I-21 | CCR5-654 | 85% | ND | 65% | 45% | 47% | 35% |
| RNA-I-22 | CD4-563 | ND | 95% | 98% | 100% | 89% | 28% |
| RNA-I-25 | CCR5-982 | 100% | ND | 0% | 36% | 0% | 23% |
| RNA-I-26 | CD4-1175 | ND | 0% | 96% | 86% | 89% | 50% |
| RNA-I-27 | CCR5-1170 | 85% | ND | 49% | 50% | 22% | 38% |
| RNA-I-28 | CD4-569 | ND | 73% | 0% | 45% | 22% | 48% |
| RNA-I-29 | RANTES Protein | 98% | ND | 0% | 14% | 20% | 18% |
| RNA-I-30 | CCR5-1301 + RANTES Protein | 96% | ND | 27% | 14% | 35% | 18% |

Note:

The second header row is either sample volume (µL) or dilution; the third header row is HIV-1 virus type.

The results do indicate that CCR5_siRNAs, CCR5-654, CCR5-982, CCR5-1170 and CCR5-1301 nanosomes show efficacy against both CCR5 tropic HIV-1 BaL and dual-tropic HIV-1 RF viruses. Hence, these CCR5 candidates are promising and warrant further development.

While this invention has been particularly shown and described with references to specific embodiments, it will be understood by those skilled in the art that various changes in form and details may be made therein without departing from the spirit and scope of the invention as defined by the appended claims.

The invention claimed is:

1. A CCR5 (Cysteine-Cysteine Chemokine Receptor 5) siRNA (small interfering Ribonucleic Acid) gene sequence for human and monkey (*Macca mulatta*) genomes, comprising a 19-mer fragment matching 5'UTR (5' Untranslated Region), 3'UTR (3' Untranslated Region) or CDS (CoDing Sequence), the fragment having a GC (guanine-cytosine) content between 30% and 50%, wherein the seed sequence of the siRNA at positions 2-7 or 2-8 of the antisense strand is also present in miRNA (micro RNA), and wherein the siRNA has a 100% sequence homology between all human and monkey alternative transcripts and fewer than 120 13-mer hits.

2. The CCR5 siRNA gene sequence of claim 1 with positions 654, 720, 982, 1170 and 1301.

3. A CD4 (Cluster of Differentiation 4) siRNA gene sequence for human and monkey (*Macca mulatta*) genomes, comprising a 19-mer fragment matching 5'UTR, 3'UTR or CDS, the fragment having a GC content between 30% and 50%, wherein the seed sequence of the siRNA at positions 2-7 or 2-8 of the antisense strand is also present in miRNA, and wherein the siRNA has a 100% sequence homology between all human and monkey alternative transcripts and fewer than 160 13-mer hits.

4. The CD4 siRNA gene sequence of claim 3 with positions 563, 569, 844, 1159 and 1175.

5. A CXCR4 (C-X-C Chemokine Receptor type 4) siRNA gene sequence for human and monkey (*Macca mulatta*) genomes, comprising a 19-mer fragment matching 5'UTR, 3'UTR or CDS, the fragment having a GC content between 30% and 50%, wherein the seed sequence of the siRNA at positions 2-7 or 2-8 of the antisense strand is also present in miRNA, and wherein the siRNA has a 100% sequence homology between all human and monkey alternative transcripts and fewer than 160 13-mer hits.

6. A phospholipid nanosome for encapsulating the CCR5 siRNA gene sequence of claim 1.

7. The phospholipid nanosome of claim 6 comprising DPPC (1,2-dipalmitoyl-sn-glycero-3-phosphocholine) and DSPE-PEG-2000 (1,2-dipalmitoyl-sn-glycero-3-phosphoethanolamine-N-[methoxy(polyethylene glycol)-2000] (ammonium salt).

8. The phospholipid nanosome of claim 6 produced using SuperFluids Propane::Ethanol::80:20 at 3,000 psig and 40° C.

9. The phospholipid nanosome of claim 6 produced in a SuperFluids Critical Fluid Nanosomes apparatus.

10. The phospholipid nanosome of claim 6 effective in knocking down HIV-1 virus infection of cells.

11. The phospholipid nanosome of claim 6 coated with CCL5 (Chemokine Ligand 5) to allow targeting of the nanosome to cells expressing the receptor CCR5 on the surface.

12. The phospholipid nanosome of claim 6 coated with an alternative natural ligand for CCR5, comprising MIP-1α (Macrophage Inflammatory Protein-1 alpha) (aka CCL3 (Chemokine Ligand 3)), MIP-1β (Macrophage Inflammatory Protein-1 beta) (aka CCL4 (Chemokine Ligand 4)) or MCP-2 (Monocyte Chemotactic Protein-2) (aka CCL8 (Chemokine Ligand 8)), wherein the said alternative natural ligand allows targeting of the nanosome to cells expressing the receptor CCR5 on the surface.

13. The phospholipid nanosome of claim 6 coated with a small molecule inhibitor of HIV binding to CCR5 such as Maraviroc or with truncated or altered CCL5, which compete with HIV binding to CCR5 with a higher efficiency than CCL5, to allow targeting of the nanosome to cells expressing the receptor CCR5 on the surface.

14. A phospholipid nanosome for encapsulating the CD4 siRNA gene sequences of claim 3.

15. The phospholipid nanosome of claim 14, comprising DPPC (1,2-dipalmitoyl-sn-glycero-3-phosphocholine) and DSPE-PEG-2000 (1,2-dipalmitoyl-sn-glycero-3-phospho-ethanolamine-N-[methoxy(polyethylene glycol)-2000] (ammonium salt).

16. The phospholipid nanosome of claim 14 produced using SuperFluids Propane:Ethanol:: 80:20 at 3,000 psig and 40° C.

17. The phospholipid nanosome of claim 14 produced in a SuperFluids Critical Fluid Nanosomes apparatus.

18. The phospholipid nanosome of claim 14 effective in knocking down HIV-1 virus infection of cells.

19. The phospholipid nanosome of claim 14 coated with mature IL-16 (Interleukin-16) protein to allow targeting of the nanosome to cells expressing the receptor CD4 on the surface.

20. A phospholipid nanosome for encapsulating the CXCR4 siRNA gene sequences of claim 5.

21. The phospholipid nanosome of claim 20, comprising DPPC (1,2-dipalmitoyl-sn-glycero-3-phosphocholine) and DSPE-PEG-2000 (1,2-dipalmitoyl-sn-glycero-3-phospho-ethanolamine-N[methoxy(polyethylene glycol)-2000] (ammonium salt).

22. The phospholipid nanosome of claim 20 produced using SuperFluids Propane:Ethanols 80:20 at 3,000 psig and 40° C.

23. The phospholipid nanosome of claim 20 produced in a SuperFluids Critical Fluid Nanosomes apparatus.

24. The phospholipid nanosome of claim 20 effective in knocking down HIV-1 virus infection of cells.

25. The phospholipid nanosome of claim 20 coated with SDF1 (Stromal Cell-Derived Factor 1)to allow targeting of the nanosome to cells expressing the receptor CXCR4 on the surface.

26. The phospholipid nanosome of claim 20 coated with an alternate ligand for CXCR4, comprising isoforms of CXCL12 (C-X-C Motif Chemokine Ligand 12), 7 of which have been identified so far, and Plerixafor, wherein a small molecule inhibitor of CXCL12 binding to CXCR4 allows targeting of the nanosome to cells expressing the receptor CXCR4 on the surface.

* * * * *

SEQUENCE LISTING

```
<160> NUMBER OF SEQ ID NOS: 2

<210> SEQ ID NO 1
<211> LENGTH: 69
<212> TYPE: DNA
<213> ORGANISM: Homo Sapiens

<400> SEQUENCE: 1

aaggcaaccg acaccgacaa cgaaggacgc aggcacgcac ccaacagggg accaaacagc      60

caaacgccg                                                              69


<210> SEQ ID NO 2
<211> LENGTH: 74
<212> TYPE: DNA
<213> ORGANISM: Homo Sapiens

<400> SEQUENCE: 2

aagaccagaa cacacagaac acacggaaaa aagacacggg gccgaagcga aaacaggaag      60

aaaggcacag gaag                                                        74
```